(12) United States Patent
de Oliveira

(10) Patent No.: US 10,529,097 B2
(45) Date of Patent: Jan. 7, 2020

(54) METHOD AND APPARATUS FOR GENERATING A MULTI-SLICE DATA SET OF A HEART

(71) Applicant: Siemens Aktiengesellschaft, Uttenreuth (DE)

(72) Inventor: Andre de Oliveira, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 794 days.

(21) Appl. No.: 14/845,734

(22) Filed: Sep. 4, 2015

(65) Prior Publication Data
US 2016/0071292 A1 Mar. 10, 2016

(30) Foreign Application Priority Data

Sep. 5, 2014 (DE) .................. 10 2014 217 766

(51) Int. Cl.
| | |
|---|---|
| A61B 6/03 | (2006.01) |
| G06T 11/00 | (2006.01) |
| A61B 6/00 | (2006.01) |
| G06T 7/20 | (2017.01) |
| G06T 15/08 | (2011.01) |

(Continued)

(52) U.S. Cl.
CPC ............. G06T 11/008 (2013.01); A61B 6/03 (2013.01); A61B 6/503 (2013.01); G06T 7/20 (2013.01); G06T 15/08 (2013.01); A61B 8/0883 (2013.01); A61B 8/13 (2013.01); G06T 2207/10016 (2013.01); G06T 2207/10072 (2013.01); G06T 2207/20182 (2013.01);

(Continued)

(58) Field of Classification Search
CPC ............... G06T 11/008; G06T 15/08; G06T 2207/10016; G06T 2207/10072; G06T 2207/20182; G06T 2207/20221; G06T 2207/30048; G06T 2211/40; G06T 2211/412; G06T 7/20

See application file for complete search history.

(56) References Cited

U.S. PATENT DOCUMENTS

| | | |
|---|---|---|
| 4,903,704 A | 2/1990 | Van Eggermond et al. |
| 2003/0016852 A1 | 1/2003 | Kaufman et al. |

(Continued)

OTHER PUBLICATIONS

Marwick, "Methods used for the assessment of LV systolic function: common currency or tower of Babel?", Heart, vol. 99, pp. 1078-8211;(; 2013).

(Continued)

*Primary Examiner* — Mark D Remaly
(74) *Attorney, Agent, or Firm* — Schiff Hardin LLP

(57) ABSTRACT

In a method and apparatus for generating a three-dimensional multi-slice data set of a heart, a first image sequence with a number of two-dimensional images is acquired in a first slice of the heart during a duration of at least one heartbeat interval, and a second image sequence with a number of two-dimensional images is acquired in a second slice of the heart during the duration of a number of heartbeat intervals. The second image sequence is excised by selecting the two-dimensional images thereof that lie in a heartbeat interval closest to the duration of the heartbeat interval in the first slice. The three-dimensional multi-slice data set is generated by combining the first image sequence and the excised second image sequence.

16 Claims, 3 Drawing Sheets

(51) Int. Cl.
*A61B 8/08* (2006.01)
*A61B 8/13* (2006.01)
(52) U.S. Cl.
CPC .............. *G06T 2207/20221* (2013.01); *G06T 2207/30048* (2013.01); *G06T 2211/40* (2013.01)

(56) References Cited

U.S. PATENT DOCUMENTS

2008/0091171 A1* 4/2008 Strommer ................ A61B 5/06
                                                                                    604/528
2012/0078097 A1* 3/2012 Wang ..................... A61B 8/483
                                                                                    600/437

OTHER PUBLICATIONS

Myerson et al., "Cardiovascular magnetic resonance", ISBN 978-0-19-954957-3, Chapter 5. (Ventricular function assessment), pp. 146-147.
Leeson "Cardiovascular Imaging", ISBN 978-0-19-956845-1, Chapter 3 (Left ventricular function), pp. 112-113.

* cited by examiner

METHOD AND APPARATUS FOR GENERATING A MULTI-SLICE DATA SET OF A HEART

BACKGROUND OF THE INVENTION

Field of the Invention

The present invention concerns a method for generating a three-dimensional multi-slice data set of a heart, and a tomography apparatus for generating a three-dimensional multi-slice data set of a heart.

Description of the Prior Art

Two methods of acquiring moving images of a heart and calculating a heart function therefrom currently exist in cardiac magnetic resonance tomography (MRI—Magnetic Resonance Imaging). With retrospective gating, the heartbeat frequency of the patient barely changes during the measurement time, so that a reconstruction of an average heartbeat cycle is enabled. This average heartbeat cycle effectively reproduces the typical heartbeat of the patient. The other basic method is prospective gating, which is used for patients whose heartbeat frequency changes during the acquisition duration, since the changes in the interval duration can generate artifacts during retrospective gating. Although prospective gating is the sole solution for patients with arrhythmic heartbeats, this method is infrequently used because of its lower resolution compared with retrospective gating.

New acquisition methods, such as for instance iterative reconstruction, allow a comparable acquisition resolution to that which is currently possible with retrospective gating. A further factor with prospective gating is, however, that the heart function cannot be reliably calculated with the acquisition of a single heartbeat, since the heartbeat has a different duration for each recorded individual slice of the heartbeat, which results in different function results. In these cases, the examination results depend to a high degree on the experience and subjective estimation of the radiologist or cardiologist.

U.S. Pat. No. 4,903,704 disclosed a method in which the acquisition of data is stopped upon the occurrence of irregularities in the heartbeat. After a waiting time of several heartbeats, the acquisition of data is resumed.

SUMMARY OF THE INVENTION

An object of the present invention is to improve the resolution of three-dimensional recordings (data set acquisitions) of the heart in patients whose heartbeat intervals are arrhythmic.

According to a first aspect of the invention, this object is achieved by a method for generating a three-dimensional multi-slice data set of a heart, having the following steps. A first image sequence is acquired that includes several two-dimensional images in a first slice of the heart during a duration of at least one heartbeat interval. A second image sequence is acquired that includes a number of two-dimensional images in a second slice of the heart during the duration of a number of heartbeat intervals. The second image sequence is excised by selecting therefrom the two-dimensional images that lie in a heartbeat interval that has the duration closest to the duration of the heartbeat interval of the first slice. A three-dimensional multi-slice data set is generated by combining the first image sequence and the excised second image sequence. When this method is applied to multiple slices, the volume of the heart can be reconstructed over a large scale. As a result, the advantage is achieved that heartbeats with similar heartbeat intervals are selected for the different slices and an arrhythmia of the heartbeat can be balanced out. An automatic functional calculation of the heart helps physicians to better assess the position of patients who are suffering heart arrhythmia.

In an embodiment of the method, the method includes the step of determining the duration of one of the heartbeat intervals by recording an electrocardiogram during the acquisition of the first image sequence and/or the second image sequence. As a result, the advantage is achieved such that the duration of the heartbeat interval can be determined easily.

In a further embodiment of the method, the duration of the heartbeat interval is determined on the basis of the temporal distance between two consecutive waves of the electrocardiogram. The technical advantage is achieved that the duration of the heartbeat intervals can be determined precisely.

In a further embodiment of the method, the first wave of the consecutive waves is determined on the basis of the highest signal value of the electrocardiogram during a predetermined time frame. This achieves the advantage that a precise starting point for determining the duration of the heartbeat interval is found in a simple manner.

In another embodiment of the method, the second wave of the consecutive eaves is determined on the basis of a predetermined maximum deviation from the highest signal value of the first wave. This achieves the advantage that the subsequent second wave can be defined with high precision.

In a further embodiment of the method, the second wave is determined on the basis of a predetermined minimum deviation from the first wave. The advantage is likewise achieved such that the subsequent second wave can be defined with high precision.

In a further embodiment of the method, the data of the first image sequence and the data of the second image sequence are stored in a data memory together with the data of the electrocardiogram. The image sequences then can be post-processed by operation of a data processing system.

In a further embodiment of the method, the method includes the step of subtracting the duration of the heartbeat interval while acquiring data in the first slice from the duration of the heartbeat interval while acquiring data in the second slice. This allows an absolute value to be determined that specifies how close the heartbeat interval is to the heartbeat interval that has been determined in the first slice.

In a further embodiment of the method, a heart function is calculated on the basis of the three-dimensional multi-slice data set. This allows a precise prediction to be made with respect to the heart function or pump function.

In a further embodiment of the method, the first and/or second image sequence is acquired along a longitudinal axis or a short axis of the heart. This allows recordings to be obtained with a high resolution.

In a further embodiment of the method, the first image sequence is acquired during a duration of a number of heartbeat intervals. This allows a heartbeat interval with a mean or suitable duration can be selected from the number of heartbeat intervals.

In a further embodiment of the method, a heartbeat interval with the shortest duration and a heartbeat interval with the longest duration are determined while recording in the first slice. This allows the shortest and the longest heartbeat interval to be reconstructed in each case three-dimensionally by a further tomography.

In a further embodiment of the method, a three-dimensional multi-slice data set is generated for the heartbeat interval with the shortest duration and a three-dimensional multi-slice data set is generated for the heartbeat interval with the longest duration. This allows precise conclusions relating to the heart function to be obtained on the basis of the two multi-slice data sets.

In another embodiment of the method, the method for generating a three-dimensional multi-slice data set is any of a computed tomography method, a magnetic resonance tomography method or an ultrasound tomography method. The most suitable imaging modality thus can be elected for use.

According to a second aspect of the invention, the aforementioned object is achieved by a tomography apparatus for generating a three-dimensional multi-slice data set of a heart, having a scanner that is operated to acquire a first image sequence with a number of two-dimensional images in a first slice of the heart during a duration of at least one heartbeat interval, and that is operated to acquire a second image sequence with a number of two-dimensional images in a second slice of the heart during the duration of a number of heartbeat intervals. A processor is configure to excise the second image sequence by selecting the two-dimensional images thereof that lie in a heartbeat interval that has a duration closest to the duration of the heartbeat interval in the first slice. An image reconstruction computer generates a three-dimensional multi-slice image by combining the first image sequence and the excised second image sequence. The same technical advantages are achieved with the apparatus as are achieved by the method according to the first aspect.

DESCRIPTION OF THE PREFERRED EMBODIMENTS

Figure 1:
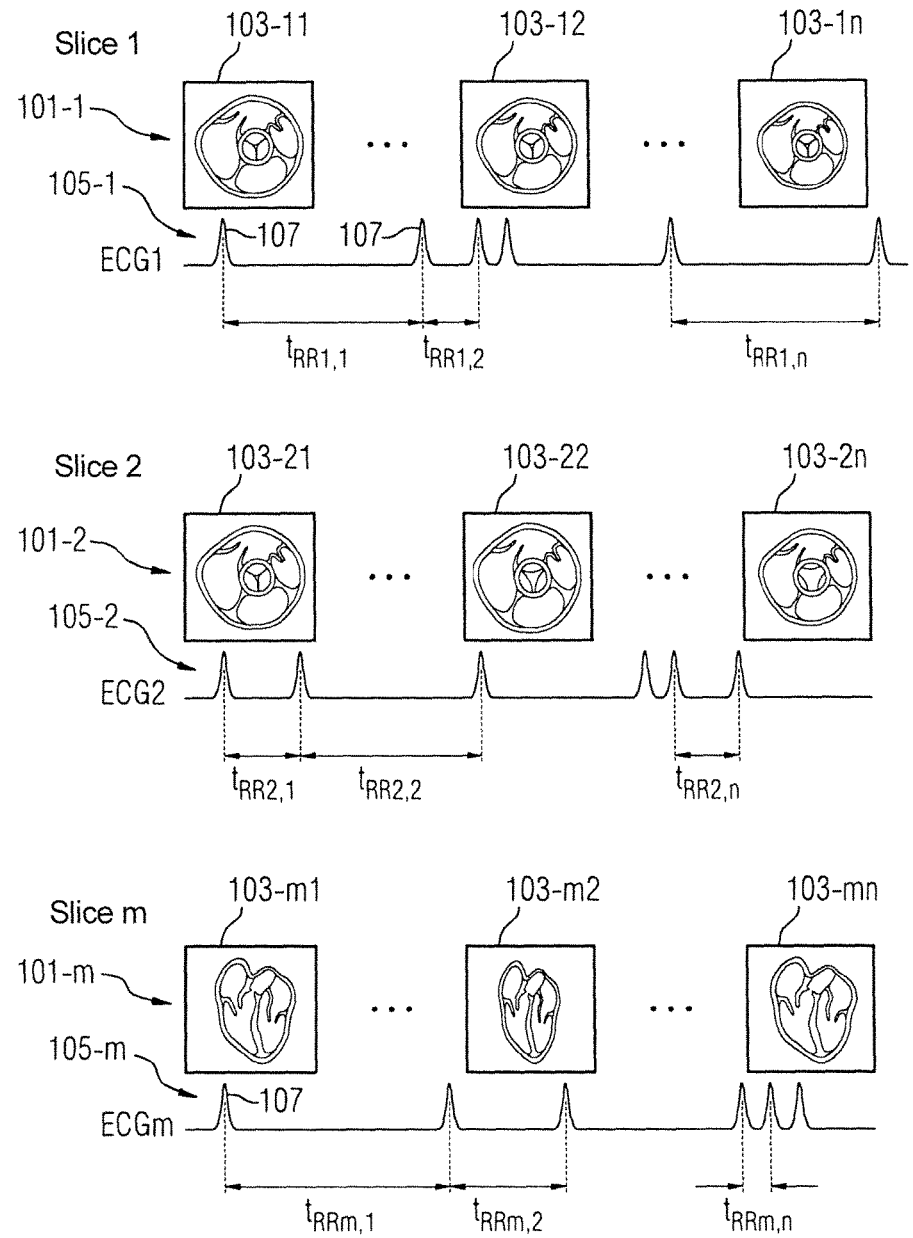
FIG. 1 shows a representation of image sequences in different cardiac slices.

FIG. 1 shows a representation of image sequences 101-1, . . . , 101-m in different slices of the heart. The image sequences 101-1, . . . , 101-m are generated by means of a tomography method, which can determine the inner spatial structure of an object and represent the same in the form of sectional images.

FIG. 1 represents the situation when acquiring MR real-time data in a number of slices using prospective gating which is obtained over several heartbeats. For each slice orientation, like for instance the short axis (SAX) or the long axis (LAX), a number of heartbeats are plotted and stored together with an electrocardiogram 105-1, . . . , 105-m. The duration trr(m, n) is the duration of the heartbeat interval (RR-interval) of the slice m for the heartbeat n.

Each of the image sequences 101-1, . . . , 101-m includes a number of two-dimensional images 103-11, . . . , 103-mn, which represent a sectional image of the heart in a certain slice. The image sequence 101-1 accordingly represents a moving recording in a first slice of the heart throughout several heartbeats. The image sequence 101-2 represents a moving image in a second slice of the heart throughout several heartbeats. The image sequence 101-m accordingly represents a moving image in an m'th slice of the heart throughout several heartbeats. The individual slices are offset in parallel to one another. The recordings of the image sequences 101 1, . . . , 101-m, are obtained one after the other in the respective slices. A sequence of moving two-dimensional images from each slice can be obtained in succession.

In addition, an electrocardiogram (EKG) 105-1, . . . , 105-m is recorded with each recording of an image sequence 101-1, . . . , 101-m. The heartbeat intervals (RR-intervals) can be identified in the respective image sequences 101-1, . . . , 101-m with the aid of the respective electrocardiogram 105-1, . . . , 105-m. With cardiac arrhythmia, the heartbeat intervals have a different duration. Therefore depending on the duration of the heartbeat interval, a different number of two-dimensional images is obtained for the heartbeat interval. An averaging or combining of the recordings from the individual slices therefore results in artifacts.

Figure 2:
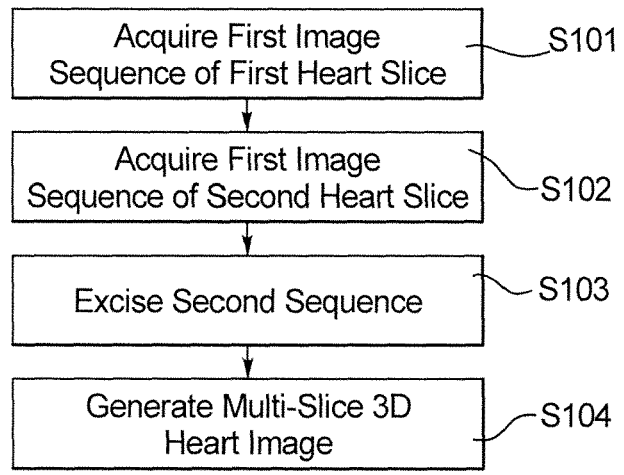
FIG. 2 is a flowchart of the method for generating a three-dimensional multi-slice data set according to the invention.

FIG. 2 shows a flowchart of a method for generating a three-dimensional multi-slice data set of the heart in the case of arrhythmia. In a first step S101, a first image sequence 101-1 with a number of two-dimensional images 103-11, . . . , 103-1n is recorded in a first slice of the heart during a duration or one or a number of heartbeat intervals. The duration of each heartbeat interval can be determined on the basis of the distance of the R-waves 107 of the electrocardiogram 105-1, . . . , 105-m. A heartbeat interval with a suitable duration is selected from the first image sequence 101-1.

In a second step S102, a second image sequence 101-2 with a number of two-dimensional images 103-21, . . . , 103-1n is then recorded in a second slice of the heart during the duration of a number of heartbeat intervals.

In a third step S103, the images 103-21, . . . , 103-2m that lie in a heartbeat interval having a duration closest to the duration of the selected heartbeat interval in the first slice, are selected from the second image sequence 101-2. The second image sequence 101-2 thus is excised to the respective heartbeat interval with a similar duration.

As a result, recordings can be obtained in the first slice and in the second slice during individual heartbeat intervals of a similar length. The steps S102 and S103 can be repeated accordingly for any number of slices.

A three-dimensional multislice recording can then be obtained in a step S104, by the respectively cut image sequences 101-1, . . . , 101-m being composed of the respective slices and combined.

Figure 3:
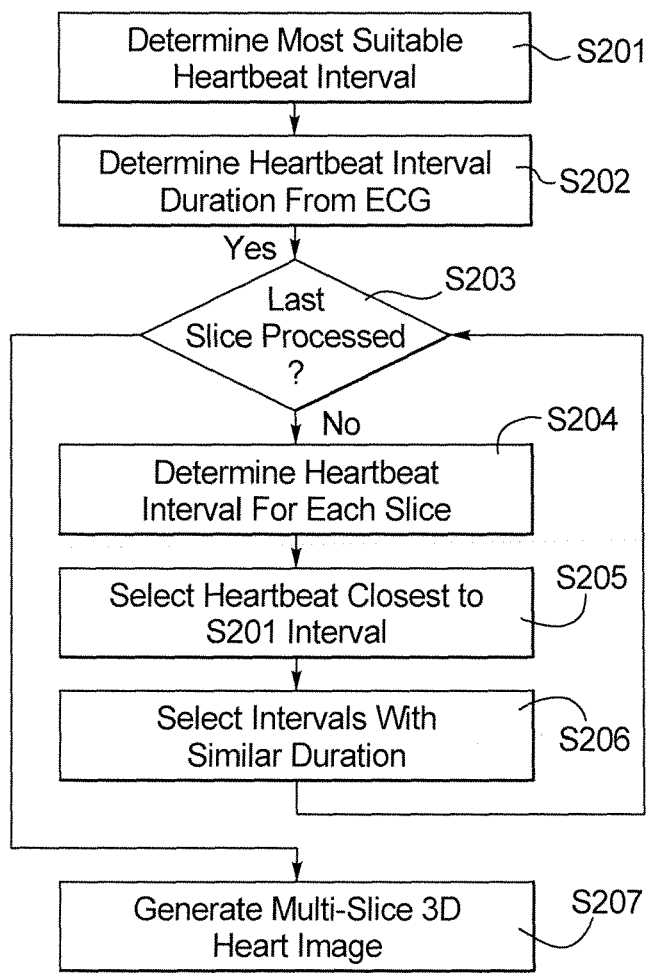
FIG. 3 is a flowchart of a further embodiment of the method for generating a three-dimensional multi-slice data set according to the invention.

FIG. 3 shows a flowchart of another embodiment of the method for generating a three-dimensional multi-slice data set. The method is used to sort and generate a multislice recording of the heart with a heartbeat. In the method, individual slices of the heart are recorded in realtime in succession during a number of heartbeats together with an electrocardiogram 105-1, . . . , 105-m. Those heartbeat intervals (RR-intervals) of a similar duration are then selected for each slice and combined to form a three-dimensional multislice data set.

In step S201, the most suitable heartbeat interval (RR interval) is selected in one predetermined slice (SAX or LAX). For instance, a user can select, in a given slice, an individual heartbeat interval which is used as reference for the next steps. Alternatively, this selection can be made by an algorithm.

In step S202, the duration of the heartbeat interval is determined from an electrocardiogram 105-1, . . . , 105-m. The duration can be obtained for instance by acquiring the waves (R-waves) 107 of the electrocardiogram 105-1, . . . , 105-m. The first wave 107 can be determined for instance as the highest signal value throughout a time frame of two seconds. The other waves 107 can be determined for instance such that waves 107 are sought which are separated at least 100 ms from the first wave 107 and have a similar intensity to the first wave 107. This can be determined for instance on the basis of a predetermined maximum deviation of +/−10-%. The duration of the heartbeat interval can generally also be determined in another way, for instance by an image analysis of the image sequences 101-1, . . . , 101-m or by acoustic pulse beats.

The condition is checked in step S203 to determine whether the last slice has been processed. If the last slice has been processed, a move is made to step S207. If the last slice has not yet been processed, a move is made to step S204.

The duration of all heartbeat intervals is determined in step S204 for each slice. This can be easily implemented by measuring the temporal distance between two consecutive waves 107 (R-waves) in the electrocardiogram 105-1, . . . , 105-m).

The heartbeat interval whose duration is closest to the heartbeat interval selected in step S201 is selected in step S205 for each slice. This can be implemented for instance by the heartbeat interval being selected for which the difference in the duration of the heartbeat interval and the duration of the heartbeat interval selected in step S201 is at its lowest. The heartbeat interval with the lowest absolute value of the difference is closest to the heartbeat interval selected in step S201, and is selected for this slice.

All selected heartbeat intervals with a similar duration are excised out of the image sequences 101-1, . . . , 101-m of the individual slices in step S206. A recording of a single heartbeat with a similar duration is as a result obtained for each slice. The data set can be stored in a data memory as separate tomographs with a number of phases.

The steps S204, S205 and S206 are repeated until the last slice has been processed.

In step S207 the individual tomographs are combined to form a series of tomographs, so that a three-dimensional multi-slice data set is produced. The multi-slice data set represents a single heartbeat. This multi-slice data set can be exported and used to calculate a heart function.

Figure 4:
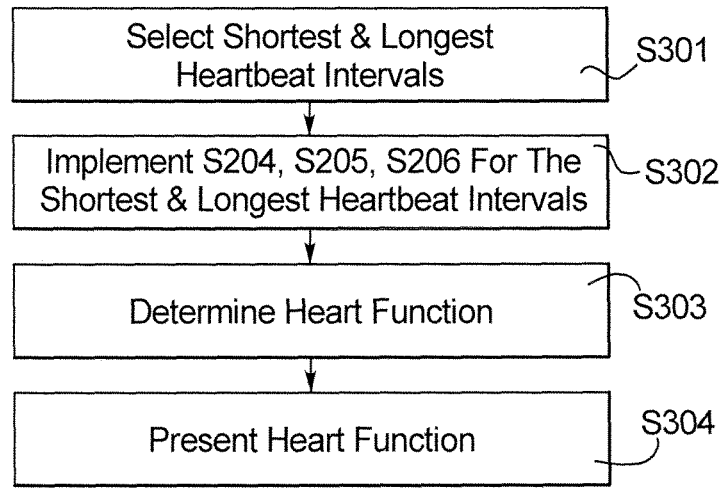
FIG. 4 is a further flowchart of an embodiment of the method according to the invention based on a shortest and a longest heartbeat intervals.

FIG. 4 shows a flowchart of an embodiment of the method based on a shortest and a longest heartbeat interval. The method can automatically select a heartbeat with the shortest (arrhythmic) and the longest (normal) heartbeat interval in order to evaluate a heart function with atrial fibrillation. The functional information is obtained from a normal and an arrhythmic heartbeat based on the method from FIG. 3.

The shortest and the longest heartbeat interval are selected for the first slice in a step S301. The duration of the heartbeat interval can be determined here in a similar manner to step S202. As soon as the individual durations are known, the shortest and the longest heartbeat interval can be selected.

In step S302, the method with the steps S204 to S206 is then implemented from the information for the shortest and the longest heartbeat interval. As a result a multi-slice recording is obtained therefrom for the shortest heartbeat interval and for the longest heartbeat interval respectively.

In step S303 a functional calculation is implemented on the basis of the multi-slice recording for the shortest heartbeat interval and the longest heartbeat interval. To this end any automatic algorithm can be used.

The functional results are indicated (presented) in step S304 for the shortest heartbeat interval and the longest heartbeat interval.

The advantages of the method lie in a functional assessment being enabled with the aid of realtime moving image data, which is obtained during several heartbeats for each slice. The method can supply cardiologists with additional information, like for instance a normal heartbeat or an arrhythmic heartbeat. The cardiologist can as a result improve their decisions about when an aggressive treatment of arrhythmia is to be performed, for instance by using an ablation.

Figure 5:
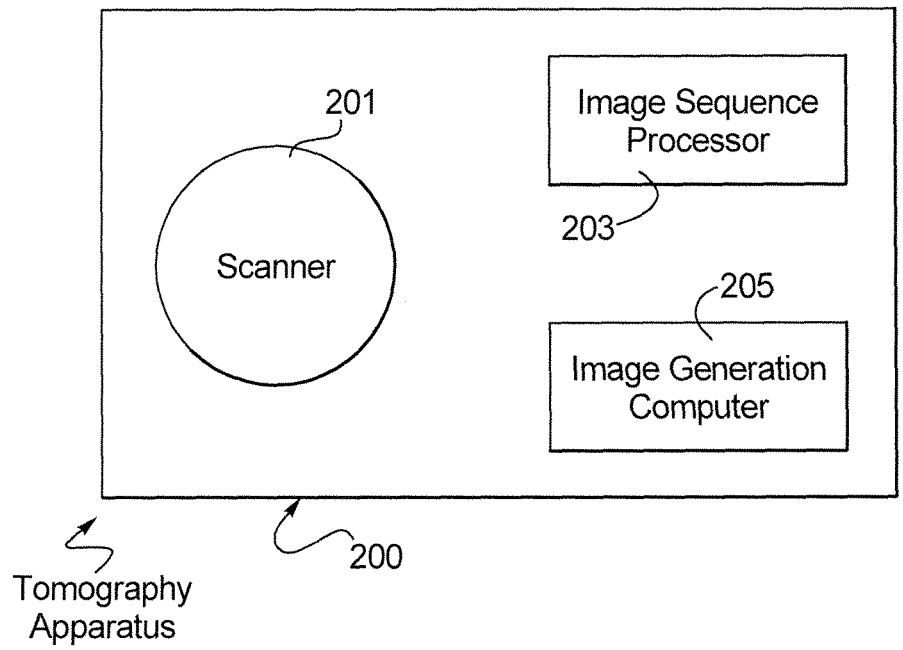
FIG. 5 is a schematic illustration of a tomography apparatus for generating a three-dimensional multi-slice image of a heart.

FIG. 5 shows a tomography apparatus 200 for generating a three-dimensional multi-slice recording of a heart. The tomography apparatus 200 is for instance a magnetic resonance tomography apparatus, a computed tomography apparatus or an ultrasound tomography apparatus.

The tomography apparatus 200 includes a scanner 201 or acquiring a first image sequence 101-1 with a number of two-dimensional images 103-11, . . . , 103-1n in a first slice of the heart during a duration of at least one heartbeat interval and a second or further image sequence 101-2 with a number of two-dimensional images 103-21, . . . , 103-2n in a second or further slice of the heart during the duration of a number of heartbeat intervals. The scanner 201 is for instance an imaging unit of the tomography apparatus 200 with a detector.

Moreover, the tomography apparatus 200 includes an image sequence processor 203 for exciting the second or further image sequence 101-2 by selecting the two-dimensional images 103-21, . . . , 103-2m, which lie in a heartbeat interval, the duration of which lies closest to the duration of the heartbeat interval in the first slice.

Furthermore, the tomography apparatus 200 includes an image generation computer 205 for generating the three-dimensional multi-slice recording by combining the first image sequence 101-1 and the excised second or further image sequence 101-2.

A computer with a microprocessor and a data memory, which is able to process the image sequences 101-1, . . . , 101m with the images 103,11, . . . , 103-1n is used for instance as the processor 203 and the image generation computer 205.

All features shown and explained in conjunction with the individual embodiments of the invention can be provided in a different combination in the inventive subject matter in order at the same time to realize its advantageous effects.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a three-dimensional, multi-slice image of a heart of a patient, comprising:

controlling a tomography scanner and an electrocardiogram detector from a computer, while a patient is situated in the tomography scanner, in order to execute a computer-controlled operation of the tomography scanner while acquiring an electrocardiogram signal from the patient;

controlling the tomography scanner from said computer in said computer-controlled operation so as to acquire a first image sequence comprising a plurality of two-dimensional images of a first slice in a first slice position of the heart of the patient, during at least one heartbeat interval of the patient as identified by the computer in said electrocardiogram signal;

controlling the tomography scanner from said computer in said computer-controlled operation in order to also acquire a second image sequence comprising a plurality of two-dimensional images of a second slice of the heart, in a second slice position that is offset from said first slice position, during a plurality of heartbeat intervals of the patient, which differ from said at least one heartbeat interval during which said first image sequence was acquired, as also identified by the computer in said electrocardiogram signal;

providing said first and second image sequences to a processor and, in said processor, automatically excising said second image sequence by selecting respective two-dimensional images of said second slice in said second image sequence that were acquired during a heartbeat interval having a duration that is closest to a duration of the heartbeat interval during which said first slice was acquired, so as to produce an excised second image sequence consisting of the selected two-dimensional images; and in said processor, generating a three-dimensional, multi-slice image of the heart by combining only said two-dimensional images in said first image sequence and said selected two-dimensional images in said excised second image sequence, and making said three-dimensional, multi-slice image available in electronic form as a data file at an output of said processor.

2. A method as claimed in claim 1 comprising determining, from said electrocardiogram, the duration of the heartbeat intervals that occur during at least one of said first image sequence and said second image sequence.

3. A method as claimed in claim 2 comprising determining said heartbeat interval as a temporal distance between two consecutive waves of said electrocardiogram.

4. A method as claimed in claim 3 comprising determining a first of said two consecutive waves as being a highest signal value of said electrocardiogram that occurs during a predetermined period of time that is designated by an input into, or an algorithm used by, said computer as identified by the computer in said electrocardiogram signal.

5. A method as claimed in claim 4 comprising determining a second of said two consecutive waves as a signal value of said electrocardiogram that occurs at a predetermined maximum deviation from said highest signal value as identified by the computer in said electrocardiogram signal.

6. A method as claimed in claim 4 comprising determining a second of said two consecutive waves as occurring at a predetermined minimum distance from said highest signal value as identified by the computer in said electrocardiogram signal.

7. A method as claimed in claim 2 comprising storing said first image sequence and said second image sequence in a memory together with said electrocardiogram.

8. A method as claimed in claim 1 comprising subtracting the duration of the heartbeat interval during which said first slice was acquired, from the duration of the heartbeat interval said two-dimensional images of said second slice were acquired.

9. A method as claimed in claim 1 comprising, in said processor, calculating a heart function of said heart from said three-dimensional, multi-slice image.

10. A method as claimed in claim 1 comprising acquiring at least one of said first image sequence and said second image sequence along a longitudinal axis of the heart.

11. A method as claimed in claim 1 comprising acquiring at least one of said first image sequence and said second image sequence along a short axis of the heart.

12. A method as claimed in claim 1 comprising acquiring said first image sequence during a plurality of heartbeat intervals.

13. A method as claimed in claim 12 comprising, while acquiring said first slice, determining a heartbeat interval, among said plurality of heartbeat intervals, that has a shortest duration, and a heartbeat interval, among said plurality of heartbeat intervals, that has a longest duration.

14. A method as claimed in claim 13 comprising generating said three-dimensional, multi-slice image for said heartbeat interval having the shortest duration, and generating another three-dimensional multi-slice image for the heartbeat interval having the longest duration.

15. A method as claimed in claim 1 comprising operating said tomography scanner to acquire tomographic data representing said first image sequence and said second image sequence from the group consisting of computed tomography data, magnetic resonance tomography data, and ultrasound tomography data.

16. A tomography apparatus for generating a three-dimensional, multi-slice image of a heart of a patient, comprising:

a tomography scanner;

an electrocardiogram detector that detects an electrocardiogram signal from a patient situated in the tomography scanner;

a control computer configured to operate said tomography scanner, while the patient is situated therein, to acquire a first image sequence comprising a plurality of two-dimensional images of a first slice in a first slice position of the heart of the patient, during at least one heartbeat interval of the patient as identified by the computer in said electrocardiogram signal;

said control computer being configured to operate the tomography scanner to acquire a second image sequence comprising a plurality of two-dimensional images of a second slice of the heart, in a second slice position that is offset from said first slice position, during a plurality of heartbeat intervals of the patient, which differ from said at least one heartbeat interval during which said first image sequence was acquired, as also identified by the computer in said electrocardiogram signal;

a processor provided with said first and second image sequences, said processor being configured to automatically excise said second image sequence by selecting respective two-dimensional images of said second slice in said second image sequence that were acquired during a heartbeat interval having a duration that is closest to a duration of the heartbeat interval during which said first slice was acquired, so as to produce an excised second image sequence consisting of the selected two-dimensional images; and said processor being configured to generate a three-dimensional, multi-slice image of the heart by combining only said two-dimensional images in said first image sequence and said selected two-dimensional images in said excised second image sequence, and to make said three-dimensional, multi-slice image available in electronic form as a data file at an output of said processor.

* * * * *